United States Patent [19]

Hodorek

[11] Patent Number: 4,997,445
[45] Date of Patent: Mar. 5, 1991

[54] METAL-BACKED PROSTHETIC IMPLANT WITH ENHANCED BONDING OF POLYETHYLENE PORTION TO METAL BASE

[75] Inventor: Robert A. Hodorek, Warsaw, Ind.

[73] Assignee: Zimmer, Inc., Warsaw, Ind.

[21] Appl. No.: 447,757

[22] Filed: Dec. 8, 1989

[51] Int. Cl.⁵ .............................................. A61F 00/00
[52] U.S. Cl. .......................................... 623/16; 623/18
[58] Field of Search ....................... 623/16, 18, 20, 22, 623/23, 66

[56] References Cited

U.S. PATENT DOCUMENTS

| | | | |
|---|---|---|---|
| 3,506,982 | 4/1970 | Steffee | 3/1 |
| 3,605,123 | 9/1971 | Hahn | 3/1 |
| 3,720,996 | 3/1973 | Tschermak | 29/527.1 |
| 3,855,638 | 12/1974 | Pilliar | 3/1 |
| 3,906,550 | 9/1975 | Rostoker et al. | 3/1.912 |
| 4,007,494 | 2/1977 | Sauer | 3/1.9 |
| 4,205,400 | 6/1980 | Shen et al. | 3/1.91 |
| 4,207,627 | 6/1980 | Cloutier | 3/1.911 |
| 4,213,816 | 7/1980 | Morris | 156/245 |
| 4,454,612 | 6/1984 | McDaniel et al. | 3/1.913 |
| 4,479,271 | 10/1984 | Bolesky et al. | 3/1.911 |
| 4,501,031 | 2/1985 | McDaniel et al. | 3/1.911 |
| 4,589,883 | 5/1986 | Kenna | 623/22 |
| 4,636,219 | 1/1987 | Pratt et al. | 623/22 |
| 4,718,916 | 1/1988 | Morscher | 623/23 |
| 4,795,468 | 1/1989 | Hodorek et al. | 623/18 |
| 4,865,607 | 9/1989 | Witzel et al. | 623/20 |

FOREIGN PATENT DOCUMENTS 8030611 4/1981 United Kingdom ................. 623/16

OTHER PUBLICATIONS

Depuy, Inc. advertisement—AMK Patella—JBJS, Jul. 1989, 71-A, p. 68.
Zimmer, Inc. brochure—Multi-Radius Total Knee, Lit. No. B-273-1, 1980.
Abstract entitled, "First Expiercences With a 'Gliding Press-Fit' Femoral Stem"—Morscher, E. W.—Orthop. Dep., University of Basel, CH-4055 Basel/Switzerland-—Harrington Arthritis Research Center—pp. 45-4-5—No date available.

Primary Examiner—David J. Isabella
Attorney, Agent, or Firm—Margaret L. Geringer

[57] ABSTRACT

This invention comprises a prosthetic implant having a metal base with a layer of metallic wire screen bonded to the upper surface of the base, and further having a polyethylene portion molded about the upper surface of the base. The polyethylene portion penetrates the porous openings in the screen to enhance the securement of the polyethylene portion to the base. The screen is fully encapsulated between the metal base and the polyethylene portion. The base further includes a plurality of notches spaced around the peripheral edge. The screen layer overhangs over at least a portion of the notches. In addition, the lower surface of the base includes a porous metallic layer providing an exposed porous surface. The construction of the screen layer on the upper surface of the base is different from the construction of the porous layer on the lower surface.

12 Claims, 2 Drawing Sheets

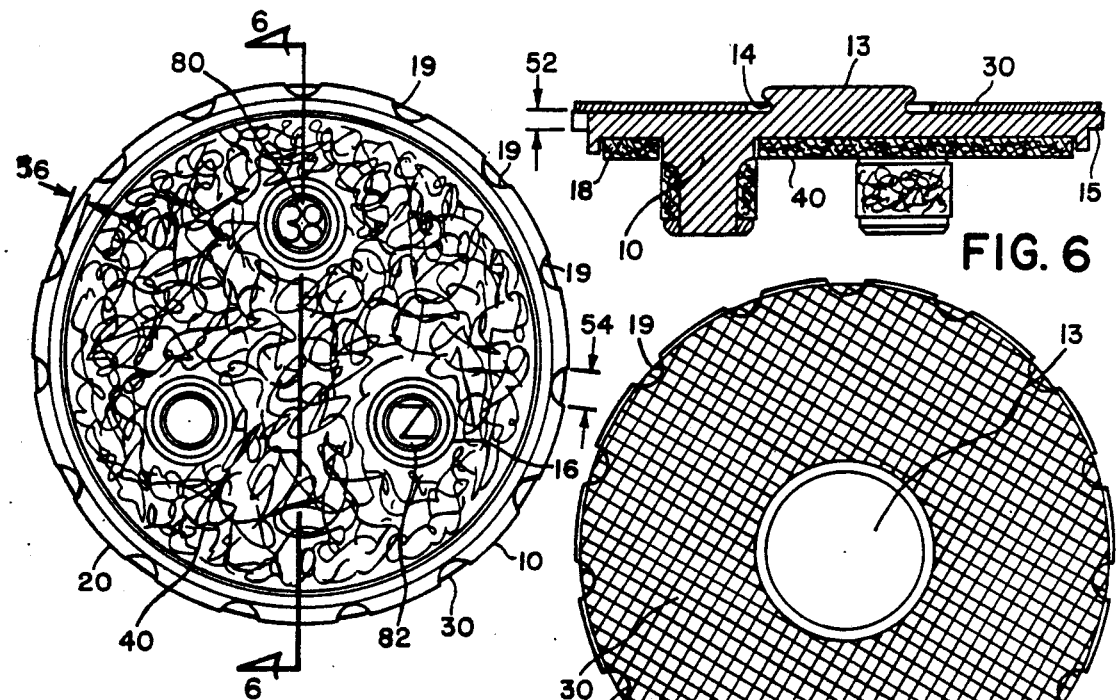
FIG. 5
FIG. 6
FIG. 7
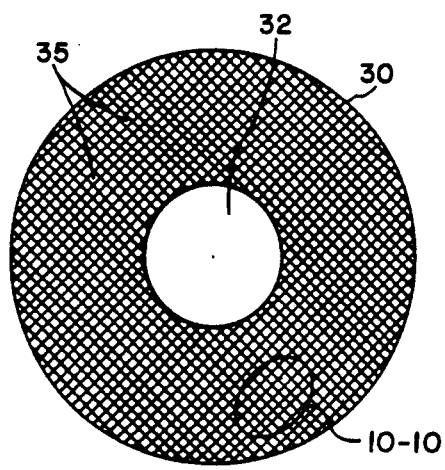
FIG. 8
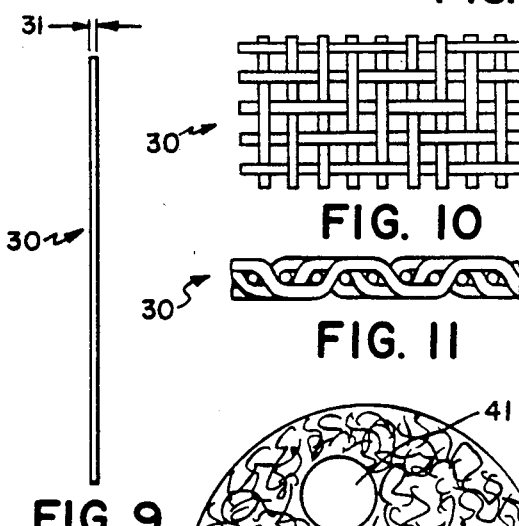
FIG. 9
FIG. 10
FIG. 11
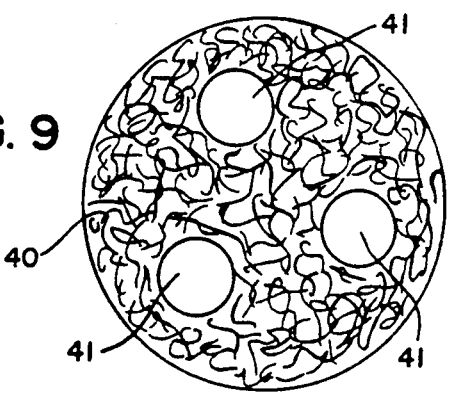
FIG. 12

METAL-BACKED PROSTHETIC IMPLANT WITH ENHANCED BONDING OF POLYETHYLENE PORTION TO METAL BASE

BACKGROUND OF THE INVENTION

The present invention relates to a prosthetic implant device, and more particularly to such implants which include a polyethylene portion secured to a metal base. This invention is particularly suitable for use as a patellar prosthesis or a tibial prosthesis although it is not limited thereto.

Heretofore, various means have been used to provide secure attachment of a polyethylene implant portion to a metal base. U.S. Pat. No. 4,501,031 to McDaniel et al. discloses a metal base which includes notches about its peripheral edge to help secure a plastic bearing portion via molding to the base. U.S. Pat. No. 4,205,400 discloses a metal base which includes tapered holes therethrough which diverge away from the upper surface and a plastic bearing portion molded to the base and through the tapered holes to secure the plastic to the metal U.S. Pat. No. 3,506,982 includes a metal anchor 3 fixed into the plastic portion 4.

In addition, a metal-backed polyethylene patella known as the AMK Patella (described in a Depuy ad ® in the July 1989 JBJS, p.68) utilizes a Porocoat porous coating on the upper surface of the metal base between the plastic and metal to lock the poly surface to the metal backing. This component also uses the Porocoat porous coating on the lower exposed surface of the base. The Porocoat coating consists of a plurality of small ball-shaped metallic particles as described by U.S. Pat. No. 3,855,638 to Pilliar.

The utilization of various porous materials to select exposed or outer surfaces of implants is well known to enhance to fixation of such outer surfaces to bone for bony ingrowth or, if a bone cement material is used for fixation, to more securely fix such outer surfaces to the bone cement. Other examples of various porous materials utilized on select outer surfaces of metal or poly implants are disclosed in U.S. Pat. Nos. 3,605,123 to Hahn; U.S. Pat. No. 3,906,550 to Rostoker et al.; U.S. Pat. No. 4,454,612 to McDaniel et al; U.S. Pat. No. 4,589,883 to Kenna; and 4,636,219 to Pratt et al. In addition, U.S. Pat. No. 4,479,271 to Bolesky et al. discloses a bottom base layer of porous fiber metal material, an intermediate metal reinforcing layer including at least one opening therein, and a top non-metal surface (such as polyethylene) which is molded to the base layer. The portion of the top polyethylene layer that is in contact with the base layer penetrates into the interstices of the porous metal material, hence securing the non-metal layer to the porous metal base layer.

U.S. Pat. No. 3,720,996 to Tschermak discloses a method of producing a tight connection between a synthetic body and a metal body which comprises inserting a porous sintered metal body into the synthetic body and then pressing them together so the plastic of the synthetic body penetrates the pores of the sintered metal body, and then connecting an additional metal body to the exposed portion of the porous sintered metal body.

U.S Pat. No. 4,007,494 to Sauer discloses a bone cap comprising a porous body adapted for bone ingrowth that is partially covered by a coating of non-porous biocompatible material such as polyethylene.

U.S. Pat. No. 4,213,816 to Morris discloses a method for bonding a porous coating of polymeric material to a rigid structural member that employs an intermediate substrate layer of material that is chemically compatible with the polymeric material, but has a lower melting temperature so as to flow into the pores of the polymeric material.

In addition, it is noted that it is known in the art of implants to separately manufacture a polyethylene portion and a metal portion and subsequently attach them by various mechanical means of locking. Often these separately manufactured poly and metal components enable the poly portion to be removably secured to the metal base. Examples of such devices are disclosed in U.S. Pat. Nos 4,795,468 to Hodorek et al. and U.S. Pat. No. 4,207,627 to Cloutier. However, it is not the intention of the present invention to address such removable attachment features, but rather to address the permanent interlock of a plastic portion to a metal portion.

OBJECTS OF THE INVENTION

A principal of the invention is to provide a metal-backed prosthetic implant which provides an enhanced, secure attachment of the polyethylene portion to the metal base.

Another object of the invention is to provide such an attachment which helps to lessen stress risers in the implant.

A further object of the invention is to optimize the attachment of the polyethylene portion to the metal base by utilizing a porous screen layer therebetween, while optimizing the outer exposed attachment surface of the metal base with a porous surface different from that of the screen layer.

A still further object of the invention is to provide means for enhancing the attachment of the poly to the metal base which is simple to manufacture, yet highly effective.

SUMMARY OF THE INVENTION

This invention comprises a prosthetic implant having a metal base with a layer of metallic wire screen bonded to the upper surface of the base, and further having a polyethylene portion molded about the upper surface of the base. The polyethylene portion penetrates the porous openings in the screen to enhance the securement of the polyethylene portion to the base. The screen is fully encapsulated between the metal base and the polyethylene portion. The base further includes a plurality of notches spaced around the peripheral edge. The screen layer overhangs over at least a portion of the notches. In addition, the lower surface of the base includes a porous metallic layer providing an exposed porous surface. The construction of the screen layer on the upper surface of the base is different from the construction of the porous layer on the lower surface.

BRIEF DESCRIPTION OF THE DRAWINGS

These features and objects of the invention as well as others, will become apparent to those skilled in the art by referring to the accompanying drawings:

FIG. 5 is a bottom plan view of the patellar component of FIG. 2, without the polyethylene portion 3 included;

FIG. 6 is a cross-sectional view taken along lines 6-6 of FIG. 5;

FIG. 7 is a top plan view of the component of FIG. 5;

FIG. 8 is a plan view of the screen layer 30 of FIG. 7;

FIG. 9 is a side elevational view of the screen layer of FIG. 8;

FIG. 10 is an enlarged detail view of the screen layer taken at 10-10 of FIG. 8;

FIG. 11 is a side view of the screen layer of FIG. 10; and

FIG. 12 is a plan view of the porous external layer 40 of FIG. 5.

DETAILED DESCRIPTION OF THE INVENTION

Figure 1:
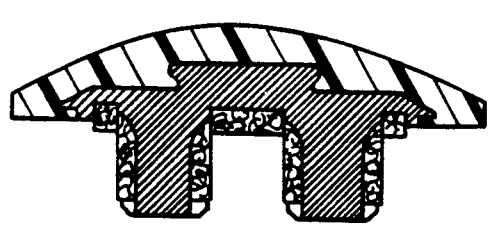
FIG. 1 is a cross-sectional view of a prior art patellar component which does not include any porous surface between the metal base and the polyethylene portion.
Figure 2:
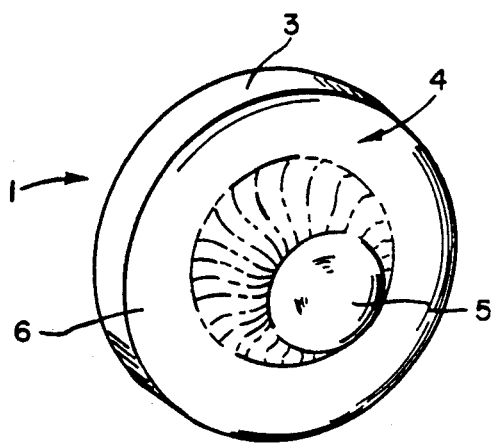
FIG. 2 is a perspective view of the top surface of a patellar component according to the present invention.
Figure 3:
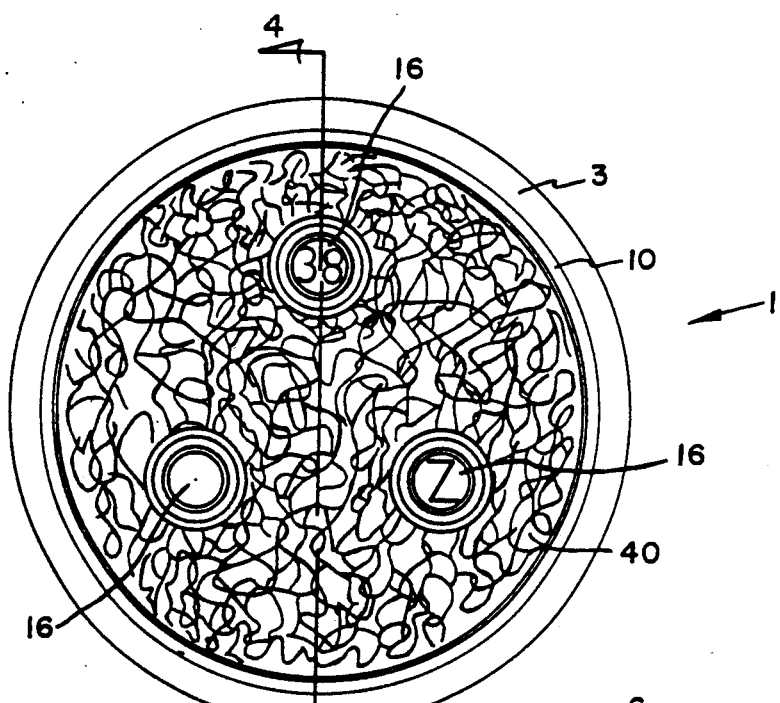
FIG. 3 is a bottom plan view of the patellar component of FIG. 2.
Figure 4:
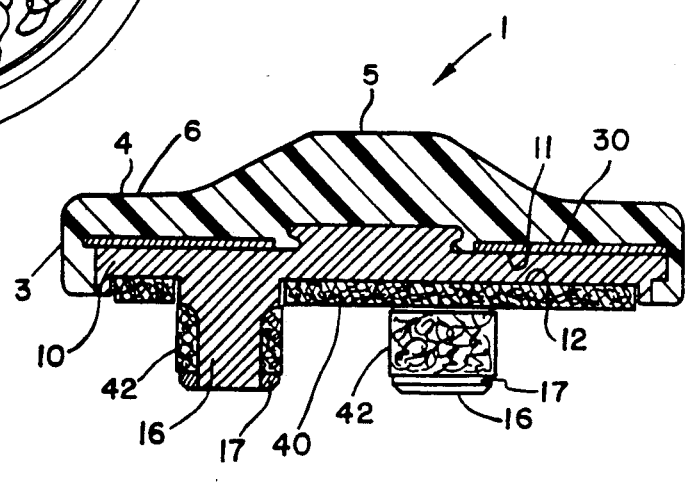
FIG. 4 is a cross sectional view of the patellar component taken along lines 4—4 of FIG. 3.

FIGS. 2-12 illustrate a particularly advantageous embodiment of a prosthetic implant according to the present invention. The invention will be described with reference to a patellar prosthetic implant and is particularly suitable as such. However, it is understood that the principles of the invention may be suitable for other implants utilizing a polyethylene portion connected to a metal base, such as a tibial component, as well as others.

The patellar prosthetic implant 1 of FIGS. 2-12 includes a metal base 10 having an upper surface 11 and a lower surface 12. The implant 1 further includes a layer of metallic wire screen 30 bonded to the upper surface 11 of the base 10. The screen 30 includes a plurality of porous openings 35 therein. The implant further includes a polyethylene portion 3 molded about the upper surface 11 of the base 10. The polyethylene portion 3 penetrates the porous openings in the screen 30 to enhance the securement of the polyethylene portion to the base 10. The screen 30 is fully encapsulated between the metal base 10 and the polyethylene portion 3. The polyethylene portion 3 includes a top surface 4 which may be any suitable articulating surface, such as that shown, which includes a central raised portion 5 and surrounding contact area 6.

The metal base 10 includes a peripheral edge 20 which includes a plurality of notches 19 spaced apart from each other around the peripheral edge 20. The notches 19 provide interdigitation between the polyethylene portion 3 and the base 4, since the poly fills the notches 19. This helps resist rotational forces, and thus helps to further secure the poly portion 3 to the base 10. The screen layer 30 extends or overhangs over at least a portion of the notches 19 as shown in FIGS. 5-7. The extension of the screen 30 over the notches 19 helps to prevent stress risers which could occur and cushions the forces seen at the notches 19.

The upper surface 11 of the base 10 further includes a raised portion 13 including an undercut ledge 14 thereabout. The raised portion 13 does not include any screen 30 (or other porous material) thereon. The molded polyethylene portion 30 thus extends under the undercut ledge 14 of the raised portion 13 to further enhance the securement of the poly portion 3 to the base 10. The raised portion 13 in the base 10 supplies resistance to shear forces, as well as tensile forces, since it is undercut.

The peripheral edge 20 also further includes an undercut ledge 15 thereabout. The molded polyethylene portion extends under the undercut ledge 15 of the peripheral edge 20 to further enhance the securement of the poly portion 3 to the base 10.

The implant 1 may also include a layer of porous metallic material 40 bonded to the lower surface 12 of the base 10. The construction of the screen layer 30 on the upper surface 11 is different from the construction of the porous metallic layer 40 on the lower surface 12. The layer 30 is a thin screen layer in which the construction comprises uniformly arranged wires with uniformly spaced openings 35 therebetween the substantially uniform pattern of wires. Although other substantially uniform patterns of wire screen may be utilized, a particularly advantageous weave pattern is a "twill" weave which is shown in the detail of FIGS. 10-11. The twill weave is a known weave pattern that goes under two wires/over two wires/under two wires/over two wires, etc. (as opposed to a standard weave which goes over/under/over/under, etc. With the twill weave, as shown in FIGS. 10-11, each shute wire typically passes over two warp wires and under two, producing square openings. Twill weave can be made from a variety of diameter wires, thereby obtaining varied requirements for strength, density, or corrosion resistance. The twill weave is advantageous for use with the present invention because it provides increased area for the poly to "reach" or flow beneath the wire diameter and supply interlock and tensile resistance.

The screen 30 is bonded to the metal base 10 by sintering, or other suitable metallic bonding means. However, before sintering, the metal wire screen 30 is compressed to create "flats" (rather than rounded wire surfaces) to increase the contact area between the screen 30 and the metal base 10. The screen is also flattened so that stress risers are not introduced beneath the high load areas. The flattened screen greatly enhances the metallic bond strength between the screen 30 and base 10. Since there are many small bonds capturing and supporting the poly 3 (which is molded to the bonded base 10 and screen 30), regardless of where the load may be applied, this construction resists giving the poly the opportunity to flow radially at the plate interface. Since this local area of poly 3 beneath the load is held firmly, overall deformation of the poly 3 is significantly reduced, thereby enhancing the performance and integrity of the component.

In contrast to the substantially uniform wire pattern of the screen 30, the porous layer 40 on the lower surface 12 of the base 10 is a metal wire mesh member in which compressed wires are bonded together in a random arrangement with randomly spaced openings therebetween A particularly suitable type of randomly patterned wires is a type such as that described in U.S. Pat. No. 3,906,550 to Rostoker et al. (mentioned above in Background section). This wire is prekinked and then molded or compressed into the desired shape which shape produces a porous layer such as 40 having a construction which includes randomly arranged and compressed wires and randomly spaced openings therebetween. The compressed wires of layer 40 are bonded together and to the base by a suitable metallic bonding means such as sintering or diffusion bonding, thus metallurgically bonding the wires to each other at their points of contact and to the metal base at the points of contact with the base 10. This type of porous surface 40 is particularly suitable for implantation into bone without the use of bone cement, so that the bone surfaces contacting the exposed porous surface, such as 40, will enable bone to grow into the porous surface to secure the implant to the bone (not shown) If used with bone cement, the bone cement can securely interlock into the porous surface 40.

Thus, the construction for porous surface 40 is particularly suitable for securing the implant 1 into the body, whereas the differing construction for the screen layer 30 is particularly suitable for securing the poly 3 to the metal base 10. The typical optimum size porous opening 35 in the screen 30 is about 0.039 inches (1 mm), using a wire diameter of about 0.016 inches (0.4 mm). The wire diameter for the screen 30 has been chosen to optimize the poly and metal bonding Larger wire diameters provide increased metal bond strength, but less poly bond strength, since the pore size and poly interlock would be reduced. The poly is molded so it flows completely into the openings 35. The typical size porous opening in the porous layer 40 is about 0.015 inches (0.38 mm).

The screen layer 30 is thinner than the porous layer 40. The screen 30 is very thin so the thickness of the poly portion can be optimized. For example, the screen layer may be about 0.016 to 0.025 inches (0.4 to 0.6 mm) thick as shown in FIG. 9 at 31, whereas the porous layer 40 may suitably be 0.039 to 0.079 inches (1 to 2 mm) to allow for ingrowth of bone or penetration of bone cement. The base 10 may include a recessed portion 18 for the porous layer 40.

The discrete screen 30 includes an opening 32 therethrough as shown in FIG. 8 to allow the raised portion 13 to extend through the opening 32. The opening 32 is large enough to provide a clearance or gap between the raised portion 13 and the screen 30 to allow the molded polyethylene portion to flow freely into and extend under the undercut ledge 14 of the raised portion 13. It is noted that the embodiment shown in FIGS. 2-12 shows a single raised portion 13, which is centrally located, with a corresponding single opening 32 in screen 30; however, it is understood that, although not shown, multiple raised portions and corresponding multiple openings in the screen could be utilized in alternate embodiments in keeping with the present invention.

The notches 19 around the peripheral edge 20 of base 10 may suitably be about 0.039 inches (1 mm) in thickness (52), about 0.079 inches (2 mm) in length (54) and about 0.039 inches (1 mm) in width (56). The screen 30 overhangs the notches 19, as shown in FIGS. 5-7, with the screen 30 overhanging at least a portion of the notches 19, and in fact, substantially overhanging a majority of the length 54 and width 56 of the notches, although the screen may extend just barely short of the full width of the notches 19 as shown. Typically, the screen 30 would not extend beyond the width of the notches 19. It is understood that the extension is of a porous screen layer 30 with holes 35 throughout, thus still allowing the poly 3 to fill through the notches 19. This overhang of screen 30 over notches 19, as described, is considered an important feature, as it helps lessen the chance for stress risers in the design. Further, since the screen 30 substantially covers the metal base 10 to its peripheral edge 20 and overhangs the notches 19, and the metal base 10 extends nearly to the periphery of the entire implant 1, this helps provide support where the loads are highest.

The patella implant 1, shown in FIGS. 2-12, may additionally include a plurality of posts 16 extending from base 10 for fixation and support. The 3-post design shown resists shear stresses and prevents toggling. The posts additionally may include porous material 42 about the posts, similar to the porous material layer 40, with metallic cap portions 17 on the end of each post 16.

The base 10 of the implant 1 may be machined or cast or otherwise suitably manufactured out of any appropriate metal suitable for surgical implants, such as titanium or a titanium alloy. The wire screen 30 and porous wire layer 40 may also be made from titanium or a titanium alloy. The porous screen 30 and porous layer 40 are bonded metallurgically to the base 10 as previously described. It is noted that the screen 30 and the porous layer 40, including the porous material 42 about the posts, and the caps 17, may all be bonded to the base 10 in a single bonding operation in which these items are held together in a suitable bonding fixture (not shown). The poly portion 3, which may suitably be ultra high molecular weight polyethylene, is then molded about the upper surface 11 and peripheral edge 20 of base 10 to fully encapsulate the screen 30 between the metal base 10 and the poly portion 3. It is understood that other suitable metal or non-metal implant materials may be utilized with the present invention, as appropriate. Any suitable manufacturing methods may be utilized.

The internal construction of the patellar implant 1 is designed to maintain the integrity and shape of the patella through dynamic knee activity The metal base 10 extends nearly to the periphery of the overall implant 1 to provide support where the loads are high.

With reference to FIG. 5, it is noted that indicia 80 and 82 may be utilized on the end of posts 16, if desired. Indicia 80, as shown, indicates the prosthesis size reference, while indicia 82 indicates the manufacturer's initial. Multiple, or other component sizes may be utilized, and thus the appropriate size reference may be referenced via the appropriate indicia. Other information, if needed, could be indicated in a similar manner. This information may be etched on or otherwise indicated in accordance with typical industry practice re the marking of implants.

The prosthetic implant 1 of the present invention described herein includes a unique enhanced means of bonding or securely attaching a polyethylene portion to a metal base to provide a secure polyethylene/metal interlock therebetween. While this invention has been described and exemplified in terms of a particularly advantageous embodiment, those skilled in the art can appreciate that modifications can be made without departing from the spirit and scope of this invention.

I claim:

1. A prosthetic implant having a metal base including an upper surface and a lower surface, the implant further including a layer of metallic wire screen bonded to the upper surface of the metal base, the screen having porous openings therein, and the implant further including a polyethylene portion molded about the upper surface of the base, the polyethylene portion penetrating the porous openings in the screen to enhance the securement of the polyethylene portion to the base and wherein the screen is fully encapsulated between the metal base and the polyethylene portion, and wherein the metal base includes a peripheral edge which includes a plurality of notches spaced apart from each other around the peripheral edge, and wherein the screen layer extends and overhangs over at least a portion of the notches.

2. The implant of claim 2 wherein the lower surface includes a layer of porous metallic material bonded thereto and wherein the construction of the screen layer on the upper surface is different from the construction of the porous metallic layer on the lower surface.

3. A prosthetic implant having a metal base including an upper surface and a lower surface, the implant further including a layer of metallic wire screen bonded to the upper surface of the metal base, the screen having porous openings therein, and the implant further including a polyethylene portion molded about the upper surface of the base, the polyethylene portion penetrating the porous openings in the screen to enhance the securement of the polyethylene portion to the base and wherein the screen is fully encapsulated between the metal base and the polyethylene portion, and wherein the upper surface further includes a raised portion including an undercut ledge thereabouts, and wherein the raised portion does not include any screen thereon, and wherein the molded polyethylene portion extends under the undercut ledge of the raised portion to further enhance the securement of the polyethylene portion to the base.

4. A prosthetic implant having a metal base including an upper surface and a lower surface, the implant further including a layer of metallic wire screen bonded to the upper surface of the metal base, the screen having porous openings therein, and the implant further including a polyethylene portion molded about the upper surface of the base, the polyethylene portion penetrating the porous openings in the screen to enhance the securement of the polyethylene portion to the base and wherein the screen is fully encapsulated between the metal base and the polyethylene portion, and wherein the upper surface further includes a raised portion including an undercut ledge thereabout, and wherein the raised portion does not include any screen thereon, and wherein the molded polyethylene portion extends under the undercut ledge of the raised portion to further enhance the securement of the polyethylene portion to the base, and wherein the peripheral edge further includes an undercut ledge thereabout, and wherein the molded polyethylene portion extends under the undercut ledge of the peripheral edge to further enhance the securement of the polyethylene portion to the base.

5. The implant of claim 3 wherein the screen includes an opening means therethrough to allow the raised portion to extend through the opening means and wherein the opening means is large enough to provide a clearance or gap between the raised portion and the screen to allow the molded polyethylene portion to fully extend under the undercut ledge of the raised portion.

6. The implant of claim 1 wherein the screen is uniformly constructed using a twill weave.

7. The implant of claim 1 wherein the screen is compressed to flatten the screen and increase the contact area between the screen and the upper surface of the base.

8. A prosthetic implant having a metal base including an upper surface and a lower surface, the implant further including a first porous layer of one construction bonded to the upper surface and a second porous layer of a second construction different from the one construction, the second layer bonded to the lower surface, and the implant further including a polyethylene portion molded about the upper surface of the metal base, the polyethylene penetrating the first porous layer to enhance the securement of the polyethylene portion to the base and wherein the first porous layer is fully encapsulated between the metal base and the polyethylene portion, and wherein the second porous layer provides an exposed porous surface.

9. The implant of claim 8 wherein the one construction of the first porous layer is a screen member having substantially uniformly arranged pattern of wires and substantially uniformly spaced openings therebetween and wherein the second construction of the second porous layer is a mesh member having randomly arranged and compressed wires and randomly spaced openings therebetween.

10. The implant of claim 8 wherein the first porous layer is thinner than the second porous layer.

11. A prosthetic implant having a metal base including an upper surface and a lower surface, the implant further including a porous metallic layer bonded to the upper surface of the metal base, and the implant further including a polyethylene portion molded about the upper surface of the base, the polyethylene portion penetrating the porous layer to enhance the securement of the polyethylene portion to the base and wherein the porous layer is fully encapsulated between the metal base and the polyethylene portion, and wherein the metal base includes a peripheral edge which includes a plurality of notches spaced apart from each other around the peripheral edge, and wherein the porous layer extends and overhangs over at least a portion of the notches.

12. The implant of claim 11 wherein the notches have a width and a length and the porous layer extends over a majority of the width and length of the notches, but does not extend beyond the width of the notches.

* * * * *